United States Patent
Bull et al.

(10) Patent No.: US 8,834,840 B1
(45) Date of Patent: *Sep. 16, 2014

(54) MAGNETIC RESONANCE IMAGING OF SELF-ASSEMBLED BIOMATERIAL SCAFFOLDS

(75) Inventors: Steve R. Bull, Wilmette, IL (US); Thomas J. Meade, Wilmette, IL (US); Samuel I. Stupp, Chicago, IL (US)

(73) Assignee: Northwestern University, Evanston, IL (US)

( * ) Notice: Subject to any disclaimer, the term of this patent is extended or adjusted under 35 U.S.C. 154(b) by 1644 days.

This patent is subject to a terminal disclaimer.

(21) Appl. No.: 11/906,825

(22) Filed: Oct. 4, 2007

Related U.S. Application Data

(60) Provisional application No. 60/849,393, filed on Oct. 4, 2006, provisional application No. 60/849,534, filed on Oct. 5, 2006.

(51) Int. Cl.
| | | |
|---|---|---|
| *A61K 51/00* | (2006.01) | |
| *A61M 36/14* | (2006.01) | |
| *A61K 38/07* | (2006.01) | |
| *A61K 38/03* | (2006.01) | |

(52) U.S. Cl.
CPC *A61K 38/07* (2013.01); *A61K 38/03* (2013.01)
USPC ......... 424/1.69; 424/1.11; 424/1.65; 424/9.3; 424/9.34; 530/300; 530/328; 530/330

(58) Field of Classification Search
CPC ........... A61K 2123/00; A61K 2121/00; A61K 51/0478; A61K 51/00; A61K 51/082; A61K 51/02; A61K 51/0474; A61K 51/0482; A61K 51/06; A61K 51/065; A61K 51/04; A61K 51/0497; A61K 51/088; A61K 51/08; A61K 38/03; A61K 38/04; A61K 38/07; A61K 38/03; A61K 38/00; A61K 49/00; A61K 49/0002; A61K 49/14; A61K 49/085; A61K 49/10; A61K 49/16; A61K 49/06; A61K 49/146; C07K 7/00; C07K 7/02; C07K 7/06; C07K 7/14; C07K 5/00; C07K 5/02; C07K 5/04; C07K 5/10
USPC ............... 424/1.11, 1.65, 1.69, 9.1, 9.3, 9.34; 534/7, 10–14; 530/300, 328, 330
See application file for complete search history.

(56) References Cited

U.S. PATENT DOCUMENTS

| | | | |
|---|---|---|---|
| 4,839,464 A | 6/1989 | McCarthy et al. | |
| 4,933,441 A | 6/1990 | Gibby | |
| 5,019,646 A | 5/1991 | Furcht et al. | |
| 5,702,683 A | 12/1997 | Smith et al. | |
| 5,840,691 A | 11/1998 | Furcht et al. | |
| 5,955,343 A * | 9/1999 | Holmes et al. | 435/325 |
| 6,096,863 A | 8/2000 | Fields et al. | |
| 6,656,450 B2 | 12/2003 | Hubin et al. | |
| 7,452,679 B2 * | 11/2008 | Stupp et al. | 435/7.1 |
| 2004/0001893 A1 | 1/2004 | Stupp et al. | |
| 2005/0208589 A1 | 9/2005 | Stupp et al. | |

FOREIGN PATENT DOCUMENTS

| | | |
|---|---|---|
| WO | 2003054146 | 7/2003 |
| WO | 2003070749 | 8/2003 |
| WO | 2003084980 | 10/2003 |
| WO | 2005056039 | 6/2005 |
| WO | 2005056576 | 6/2005 |
| WO | 2006096614 | 9/2006 |

OTHER PUBLICATIONS

Bull et al (Nano Letters, 2005, vol. 5, No. 1, pp. 1-4).*
Hartgerink et al, Science, 2001, vol. 294, pp. 1684-1688.*
Caravan, P; Ellison, JJ; McMurry, TJ; Lauffer, RB. Gadolinium(III) Chelates as MRI Contrast Agents: Structure, Dynamics and Applications. Chem. Rev. 1999, 99, 2293-2352.
Lee, KY; Mooney, DJ. Hydrogels for Tissue Engineering. Chem. Rev. vol. 101, No. 7, pp. 1869-1879 (Jul. 2001).
Aime, S; Botta, M; Garino, E; Crich, SG; Giovenzana, G; Pagliarin, R; Palmisano, G; Sisti, M. Non-covalent Conjugates between Cationic Polyamino Acids and GdIII Chelates: A Route for Seeking Accumulation of MRI-Contrast Agents at Tumor Targeting Sites. Chem. Eur. J. 2000, 6, No. 14, pp. 2609-2617.
De León-Rodriguez, LM; Kovacs, Z; Dieckmann, GR; Sherry AD. Solid-Phase Synthesis of DOTA-Peptides. Chem. Eur. J. 2004, 10, 1149-1155.
Meade, TJ; Taylor, AK; Bull, Sr. New Magnetic Resonance Contrast Agents as Biochemical Reporters. Current Opinion in Neurobiology 2003, 13:597-602.
Fuchs, VR; Sox Jr, HC. Physicians' Views of the Relative Importance of Thirty Medical Innovations. Health Affairs. Sep./Oct. 2001, vol. 20, No. 5, pp. 30-42.
Li, W-H; Parigi, G; Fragai, M; Luchinat, C; Meade, TJ. Mechanistic Studies of a Calcium-Dependent MRI Contrast Agent. Inorganic Chemistry, vol. 41, No. 15, 2002, pp. 4018-4024.
Aletras, A; Barlos, K; Gatos, D; Koutsogianni, S; Mamos, P. Preparation of the very acid-sensitive Fmoc-Lys(Mtt)-OH: application in the synthesis of side-chain cyclic peptides and oligolysine cores suitable for the solid-phase assembly of MAPs and TASPs. International Journal of Peptide & Protein Research (1995), 45(5), 488-96.

(Continued)

*Primary Examiner* — D L Jones

(74) *Attorney, Agent, or Firm* — Reinhart Boerner Van Deuren s.c.

(57) ABSTRACT

Compositions and/or mixtures comprising peptide amphiphile compounds comprising one or more contrast agents, as can be used in a range of magnetic resonance imaging applications.

18 Claims, 3 Drawing Sheets

(56) References Cited

OTHER PUBLICATIONS

Cavagna, FM; Maggioni, F; Castelli, PM; Dapra, M; Imperatori, LG; Lorusso, V; Jenkins, B. Gadolinium Chelates with Weak Binding to Serum Proteins: A New Class of High-Efficiency, General Purpose Contrast Agents for Magnetic Resonance Imaging. Investigative Radiology, 32(12): pp. 780-796, Dec. 1997.

Nicolle, GM; Tóth, É; Eisenwiener, K-P; Mäcke, HR; Merbach, AE. From monomers to micelles: investigation of the parameters influencing proton relaxivity. J. Biol. Inorg. Chem. (2002) 7: 757-769.

Mäder, K; Bacic, G; Domb, A; Elmalak, 0; Langer, R; Swartz, HM. Noninvasive in Vivo Monitoring of Drug Release and Polymer Erosion from Biodegradable Polymers by EPR Spectroscopy and NMR Imaging. Journal of Pharmaceutical Sciences, vol. 86, No. 1, Jan. 1997.

Niece, KL; Hartgerink, JD; Donners, JJJM; Stupp, SI. Self-Assembly Combining Two Bioactive Peptide-Amphiphile Molecules into Nanofibers by Electrostatic Attraction. J. Am. Chem. Soc. 2003, 125, 7146-7147.

Claussen, RC; Rabatic, BM; Stupp, SI. Aqueous Self-Assembly of Unsymmetric Peptide Bolaamphiphiles into Nanofibers with Hydrophilic Cores and Surfaces. J. Am. Chem. Soc. 2003, 125, 12680-12681.

Behanna, HA; Donners JJJM; Gordon, AC; Stupp, SI. Coassembly of Amphiphiles with Opposite Peptide Polarities into Nanofibers. J. Am. Chem. Soc. 2005, 127, 1193-1200.

Wiener, E; Brechbiel, MW; Brothers, H; Magin, RL; Gansow, OA; Tomalia, DA; Lauterbur, PC. Dendrimer-based metal chelates: A new class of magnetic resonance imaging contrast agents. Magnetic Resonance in Medicine (1994), 31(1), 1-9.Abstract. DOI Oct. 1002/mrm. 1910310102.

Stroman, PW; Dorvil, J-C; Marois, Y; Poddevin, N; Guidoin, R. In Vivo Time Course Studies of the Tissue Responses to Resorbable Polylactic Acid Implants by Means of MRI. Magnetic Resonance in Medicine 42:210-214 (1999).

Bull, SR; Guler, MO; Bras, RE; Meade, TJ; Stupp, SI. Self-Assembled Peptide Amphiphile Nanofibers Conjugated to MRI Contrast Agents. Nano Letters, vol. 5, No. 1, Jan. 2005, pp. 1-4.

Guler, MO; Soukasene, S; Hulvat, JF; Stupp, SI. Presentation and Recognition of Biotin on Nanofibers Formed by Branched Peptide Amphiphiles. Nano Letters, 2005, vol. 5, No. 2, pp. 249-252.

Langer, R; Tirrell, DA. Designing materials for biology and medicine. Nature. vol. 428, Apr. 1, 2004. pp. 487-492.

Pierschbacher, MD; Ruoslahti, E. Cell attachment activity of fibronectin can be duplicated by small synthetic fragments of the molecule. Nature. vol. 309, May 3, 1984. pp. 30-33.

Zjang, S. Fabrication of novel biomaterials through molecular self-assembly. Nature Biotechnology. vol. 21, No. 10 Oct. 2003, pp. 1171-1178.

Louie, AY; Hüber, MM; Ahrens, ET; Rothbächer, U; Moats, R; Jacobs, RE; Fraser, SE; Meade, TJ. In vivo visualization of gene expression using magnetic resonance imaging. Nature Biotechnology, vol. 18 Mar. 2000, pp. 321-325.

Kohn, J. New approaches to biomaterials design. Nature Materials, vol. 3, Nov. 2004. pp. 745-747.

Högemann-Savellano, D; Bos, E; Blondet, C; Sato, F; Abe, T; Josephson, L; Weissleder, R;. Gaudet, J.; Sgroi, D; Peters, PJ; Basilion, JP. The Transferrin Receptor: A Potential Molecular Imaging Marker for Human Cancer. Neoplasia, vol. 5, No. 6. Nov./Dec. 2003, pp. 495-506.

Mäder, K; Crémmilleux, Y; Domb, AJ; Dunn, JF; Swartz, HM. In Vitro/In Vivo Comparison of Drug Release and Polymer Erosion from Biodegradable P(FAD-SA) Polyanhydrides—A Noninvasive Approach by the Combined Use of Electron Paramagnetic Resonance Spectroscopy and Nuclear Magnetic Resonance Imaging. Pharmaceutical Research, vol. 14, No. 6, 1997, pp. 820-826.

Melia, CD; Rajabi-Siahboomi, AR; Bowtell, RW. Magnetic resonance imaging of controlled release pharmaceutical dosage forms. PSTT, vol. 1, No. 1, Apr. 1998. pp. 32-39.

Hartgerink, JD; Beniash, E; Stupp, SI. Peptide-amphiphile nanofibers: A versatile scaffold for the preparation of self-assembling materials. PNAS. Apr. 16, 2002, vol. 99, No. 8, pp. 5133-5138.

Kisiday, J; Jin, M; Kurz, B.; Hung, H; Semino, C; Zhang, S; Grodzinsky, AJ. Self-assembling peptide hydrogel fosters chondrocyte extracellular matrix production and cell division: Implications for cartilage tissue repair. PNAS. Jul. 23, 2002, vol. 99, No. 15. pp. 996-10001.

Silva, GA; Czeisler, C; Niece, KL; Beniash, E; Harrington, DA; Kessler, JA, Stupp, SI. Selective Differentiation of Neural Progenitor Cells by High-Epitope Density Nanofibers. Science, 00368075, Feb. 27, 2004, vol. 303, Issue 5662.

Hartgerink, JD; Beniash, E; Stupp, SI. Self-Assembly and Mineralization of Peptide-Amphiphile Nanofibers. Science, 00368075, Nov. 23, 2001, vol. 294, Issue 5547.

Xiong, J-P, et al. Crystal Structure of the Extracellular Segment of Integrin alphaVbeta3. Science, 00368075, Oct. 12, 2001. Vol. 294, Issue 5541.

Traoré, AS; Woerley, S; Doan, VD; Mardis, Y; Guidoin, R. In Vivo Magnetic Resonance Imaging and Relaxometry Study of a Porous Hydrogel Implanted in the Trapezius Muscle of Rabbits. Tissue Engineering, vol. 6, No. 3, 2000, pp. 265-278.

Toth, E; Lothar, AE. Relaxivity of MRI Contrast Agents. Topics in Current Chemistry (2002), 221 (Contrast Agents I) 61-101.

Holmes, TC. Novel peptide-based biomaterial scaffolds for tissue engineering. Trends in Biotechnology, vol. 20, No. 1, Jan. 2002, pp. 16-21.

Tilcock, C. Delivery of contrast agents for magnetic resonance imaging, computed tomography, nuclear medicine and ultrasound. Advanced Drug Delivery Reviews 37 (1999) 33-51.

Weinmann, H-J; Brasch, RC; Press, W-R; Wesbey, GE. Characteristics of Gadolinium-DTPA Complex: A Potential NMR Contrast Agent. AJR,142:619-624, Mar. 1984.

Weissleder, R; Poss, K; Wilkinson, R; Zhou, C.; Bogdanov, A Jr. Quantitation of Slow Drug Release from an Implantable and Degradable Gentamicin Conjugate by In Vivo Magnetic Resonance Imaging. Antimicrobial Agents and Chemotherapy, Apr. 1995, p. 839-845.

Guidoin, R; Langevin, F, Basle, MF; Alarcone, C; Legrand, AP, Zhang, Z; Basse-Cathalinat, B; Franconi, JM; Douville, Y.; Baquey, C. Can Magnetic Resonance Imaging Be the Key Technique to Visualize and Investigate Endovascular Biomaterials? Artificial Cells, Blood Substitutes, and Biotechnology, vol. 32, No. 1, pp. 105-127, 2004.

Greenfield, N; Fasman, GD. Computed Circular Dichroism Spectra for the Evaluation of Protein Conformation. Biochemistry, vol. 8, No. 10, Oct. 1969, pp. 4108-4116.

Hüber, MM; Staubli, AB; Kustedjo, K; Gray MHB; Shih, J; Fraser, SE; Jacobs, RE; Meade, TJ. Fluorescently Detectable Magnetic Resonance Imaging Agents. Bioconjugate Chem. 1998, 9, 242-249.

Ladd, DL; Hollister, R; Peng, X; Wei, D; Wu, G; Delecki, D; Snow, Ra; Toner, JL; Kellar, K; Eck, J; Desai, VC; Raymond, G; Kinter, LB; Desser, TS; Rubin, DL. Polymeric Gadolinium Chelate Magnetic Resonance Imaging Contrast Agents: Design, Synthesis, and Properties. Bioconjugate Chem. 1999, 10, 361-370.

Pihlajamäki, H; Kinnunen, J; Bostman, O. In vivo monitoring of the degradation process of bioresorbable polymeric implants using magnetic resonance imaging. Biomaterials 18 (1997) 1311-1315.

\* cited by examiner

MAGNETIC RESONANCE IMAGING OF SELF-ASSEMBLED BIOMATERIAL SCAFFOLDS

This application claims priority benefit from provisional application Ser. No. 60/849,393, filed on Oct. 4, 2006 and provisional application Ser. No. 60/849,534, filed on Oct. 5, 2006, each of which is incorporated herein by reference in its entirety.

This invention was made with government support under Grant No. DE-FG02-00ER45810 awarded by the Department of Energy and Grant No. 7R01AI47003-4 awarded by the National Institutes of Health. The government has certain rights in the invention.

BACKGROUND OF THE INVENTION

Current interest in human tissue repair has prompted the development of biomaterial scaffolds where the goal is to envelop cells in an environment mimicking extracellular matrix and mediate processes such as cell proliferation and differentiation. Tissue repair in mature organisms can be crippled because many of the molecular cues present in early development are absent. Peptide sequences (epitopes) can be used to influence specific cell matrix interactions leading to tissue formation. Therefore, providing a synthetic scaffold with epitopes affords the possibility of in vivo tissue regeneration.

Nanofiber networks derived from self-assembling peptide amphiphiles ("PA's") have been used to mimic bone extracellular matrix and provide a scaffold to direct the differentiation of neural progenitor cells in vitro. PA molecules contain a peptide sequence at one terminus that is hydrophilic relative to the hydrophobic alkyl segment. The PA's charge and amphiphilic nature allows for solubility and promotes self-assembly in aqueous media into long cylindrical structures that are nanometers in diameter and up to microns in length. These supramolecular structures can form fibrous strands because of hydrogen bond formation between the amino acids of adjacent PA molecules. In one case, the β-sheet-forming sequence of LLLAAA together with the hydrophobic alkyl tail's collapse is thought to be the driving force in extended structures, rather than spherical micelles. The high aspect ratio nanofibers form a three-dimensional network trapping water, to create a self-supporting gel that is 99% water by mass. Since the hydrophilic portion of the PA contains charged amino acids and is accessible to the aqueous environment, the self-assembled nanofibers can present a high density of epitopes on the periphery of the nanofibers to interact with cells trapped within. However, to understand scaffold properties in vivo, it is necessary to elucidate the structural degradation and migration of the self-assembled materials postimplantation.

SUMMARY OF THE INVENTION

In light of the foregoing, one object of the present invention is to provide one or more peptide amphiphile contrast agent ("PACA") components useful in conjunction with various compositions or formulations comprising PA's and nanofiber networks formed therefrom for the purpose of tracking the movements of the PA's and nanofibers and elucidating their fate, thereby overcoming deficiencies and shortcomings in the art. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

Another object of the present invention is to provide various compositions or formulations further comprising one or more epitope-bearing PA's, for interaction with specifically targeted cellular receptors.

Another object of the present invention is to provide a method of using such compositions or formulations for three dimensional fate mapping by magnetic resonance imaging of tissue-engineered scaffolds with targeting of specific cellular receptors, such mapping and imaging as can be accomplished in vivo.

Other objects, features, benefits and advantages of the present invention will be apparent from this summary and descriptions of certain embodiments and will be readily apparent to those skilled in the art having knowledge of various magnetic resonance contrast agents, conventional peptide synthesis methods, epitopes specific to cellular receptors of interest in tissue repair, compositions thereof and their formulation techniques. Such objects, features, benefits and advantages will be apparent from the above as taken into conjunction with the accompanying examples, data, figures and all reasonable inferences to be drawn therefrom, alone or with consideration of the references incorporated herein.

In part, the present invention can be directed to a composition and/or mixture comprising a plurality of amphiphilic peptide compounds. Such a composition can comprise a compound comprising a peptide component and a hydrophobic component coupled to either the C-terminus or N-terminus of the peptide component; and, of such compounds, at least one branched amphiphilic peptide compound comprising a peptide component comprising at least one amino acid residue comprising a pendant amino group coupled to a non-linear portion of with respect to or branching from the peptide component, and at least one amino acid residue comprising a pendant amino group bonded, conjugated with or coupled to a chelator component of a magnetic resonance contrast agent. Without limitation, as illustrated by several representative compounds, herein, such a chelator component can be conjugated with the peptide component and/or a non-linear/branching portion thereof. In certain embodiments, at least one of the aforementioned coupling or conjugation residues can be of a naturally-occurring amino acid. In certain such embodiments, the coupling and/or conjugation residues can be of lysine.

Regardless, a conjugated contrast agent can comprise a metal ion component selected from iron, manganese and gadolinium, together with various other ionic species as would be understood by those skilled in the art to have one or more spectroscopic applications. Any such contrast agent can further comprise a ligand or chelator component capable of chelating such an ionic species in the context of an amphiphilic peptide compound. Such chelator components can include but are not limited to those referenced by acronym elsewhere herein. In certain such embodiments, a conjugated chelator component can be DOTA, used in conjunction with gadolinium ion.

Regardless of any particular contrast agent or chelator component thereof, a non-linear or branch portion of the peptide component of such an amphiphilic compound can comprise one or more bioactive epitope sequences, as can be utilized for subsequent cell and/or tissue interaction. Without limitation, such sequences can be selected from RGDS, IKVAV, YIGSR and combinations thereof. Such compositions comprising a branched amphiphilic peptide compound can be provided in an aqueous medium. Depending upon concentration, pH and/or ionic strength, such amphiphilic compounds can self-assemble to provide a micellar, whether cylindrical or spherical, configuration. As described below, a hydrogel of such a composition can be characterized under magnetic resonance spectroscopy conditions and/or imaged in a corresponding magnetic field, either in vivo or in vitro.

In part, the present invention can also be directed to a composition or mixture comprising a plurality of amphiphilic compounds of the sort discussed above, with at least one of such compounds a branched amphiphilic peptide compound comprising a peptide component comprising a gadolinium magnetic resonance contrast agent conjugated thereto with a lysine residue, and a branch portion coupled to the peptide component with a lysine residue and comprising a bioactive epitope sequence. A chelator component of such a contrast agent can be as discussed above or illustrated elsewhere herein. In certain non-limiting such embodiments, the peptide component of the branched amphiphilic compound can, without limitation, comprise residues selected from alanine, glycine, cysteine, leucine and combinations thereof. As coupled thereto, a hydrophobic component of such a branched compound can, without imitation, comprise an alkyl moiety selected from about $C_6$ to about $C_{24}$ linear alkyl moieties and about $C_6$ to about $C_{24}$ branched alkyl moieties. As illustrated below in the context of several representative branched compounds, such an alkyl moiety can be coupled to the C-terminus of the peptide component with or using a lysine residue thereof.

In part, this invention can also be directed to a branched amphiphilic peptide compound of a formula

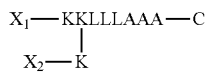

wherein $X_1$ can be a gadolinium magnetic resonance contrast agent comprising a chelator component of the sort described herein conjugated to a peptide component of such an amphiphile, $X_2$ can be a branch portion of the peptide component comprising one or more bioactive epitope sequences, and C can be a hydrophobic component comprising an alkyl moiety of the sort described herein. In certain embodiments, such a compound can be provided as a mixture or a hydrogel comprising one or more other amphiphilic peptide compounds, such other compound(s) optionally comprising a contrast agent, for characterization and/or imaging under magnetic resonance spectroscopy conditions, either in vivo or in vitro.

With respect to the compositions of the present invention, the compounds thereof can suitably comprise, consist of or consist essentially of any of the aforementioned components, epitopes, residues and/or contrast agents. Each such compound, component, epitopes, contrast agent or moiety can be compositionally distinguishable, characteristically contrasted and can be practiced in conjunction with the present invention separate and apart from another. Accordingly, it should be understood that the inventive compounds and compositions, as illustratively disclosed herein, can be practiced or utilized in the absence of any one compound, component, epitope, contrast agent and/or moiety which may or may not be disclosed, referenced or inferred herein, the absence which may or may not be specifically disclosed, referenced or inferred herein.

Compound 1 is an example of a filler PA and does not contain a Gd(III) chelate component. Compound 2 (prior art) and new compound 3 are conjugated to a Gd(III) contrast agent. For reference to the figure, the structure of a PA can be considered as having three sections: A headgroup, body, and an alkyl tail. As shown, a peptide headgroup can be composed of an epitope for specific cell interaction and is presented on the outside of the supramolecular fibers. The peptide body is structural in function and can use hydrogen bond formation between molecules as a driving force for fiber formation. The hydrophobic (e.g. palmitoyl) tail of the PA is used to drive self-assembly by initiating a hydrophobic collapse in an aqueous environment.

Figure 1:
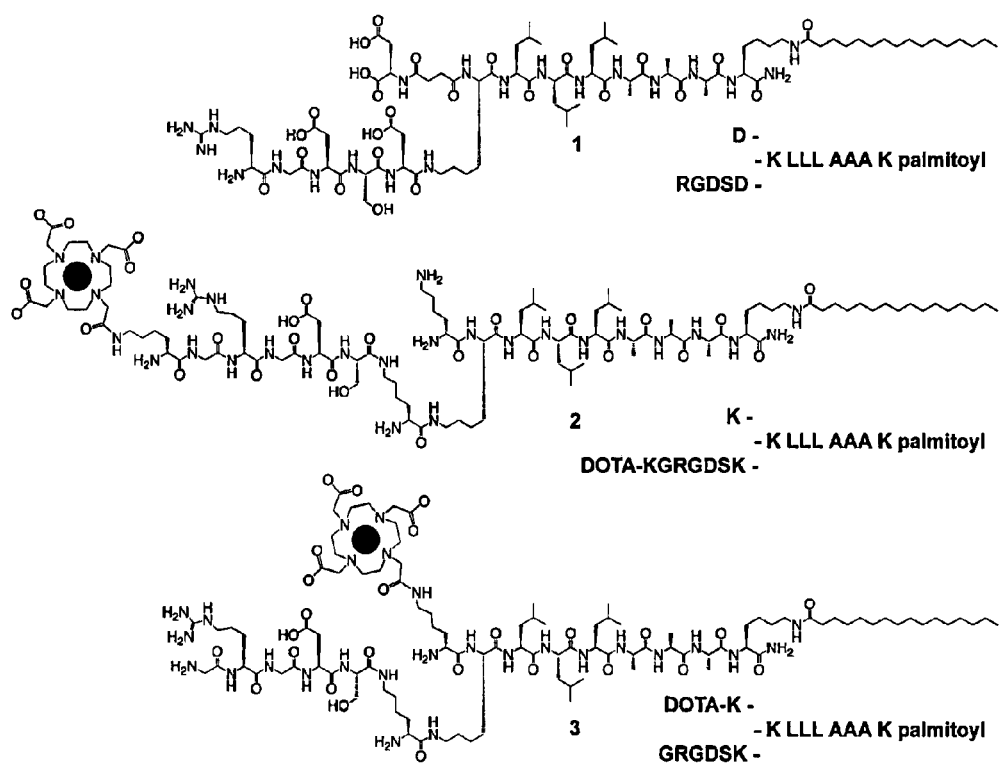
FIG. 1 shows non-limiting, representative structures of PA molecules, with the black circles representing the Gd(III) ion.
Figure 2:
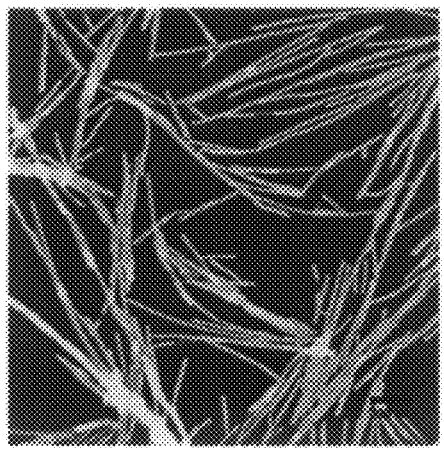

FIG. 2 provides an AFM micrograph of nanofibers formed from compound 3. This image depicts the supramolecular assembly of the PACAs into fibers. These high aspect fibers then form a network trapping water and creating a gel. The fiber heights correspond to 6.0±0.1 nm.

Figure 3:
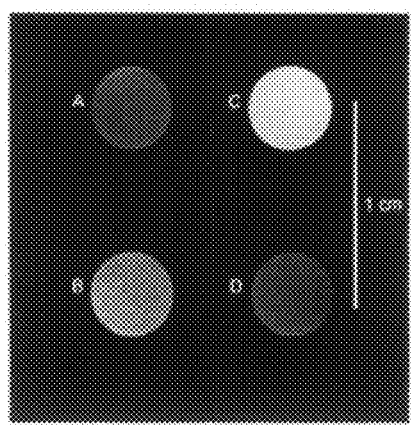

FIG. 3 provides MR images of the phantom gels formed from compound(s) 1, 1 and 2, 1 and 3, and a Gd(III) DTPA standard, corresponding to A, B, C, and D, respectively. The contrast arising from 3 is the greatest due to a change in $\tau_r$ of the Gd(III) chelator.

Figure 4:
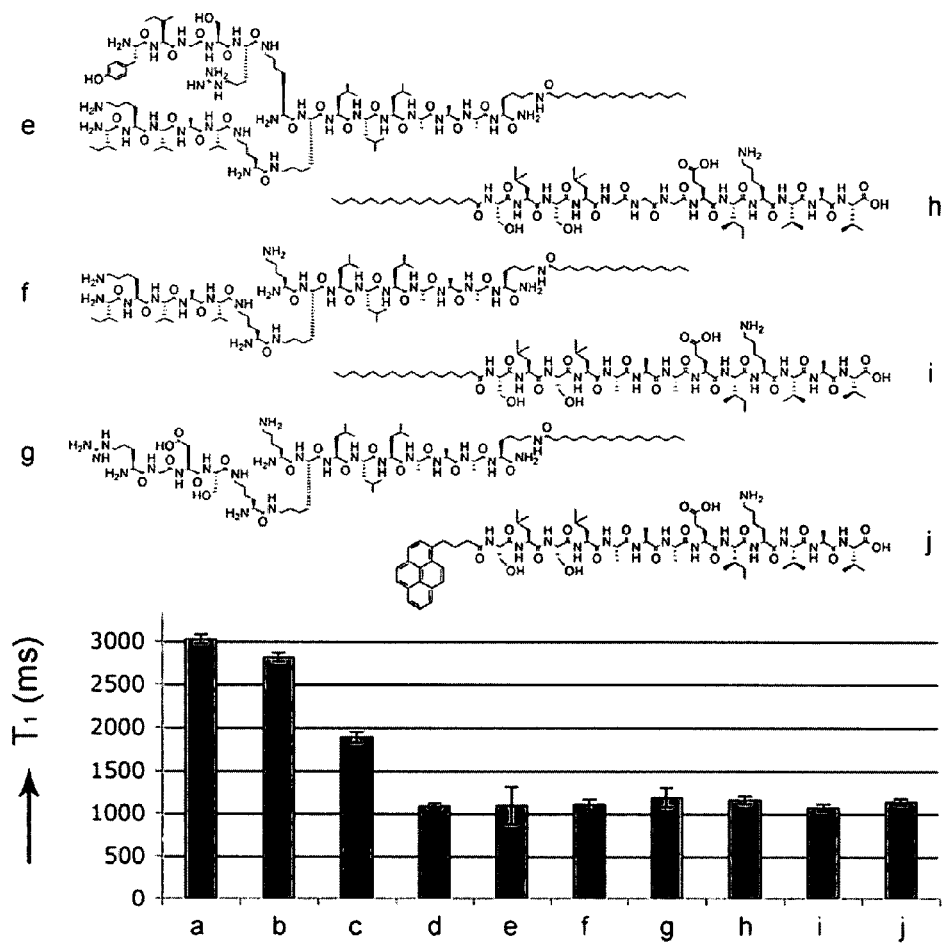

FIG. 4 depicts results of $T_1$ study of PA gels and mixed PA gels. The concentration of Gd(III) is 0.1 mM in all samples except a and the concentration of filler PA is 1 wt % in each case (all samples form self-supporting gels): a corresponds to compound 1 alone and is used as a standard, b refers to 1 mixed with DTPA, c refers to 1 mixed with compound 2, d refers to 1 mixed with compound 3, e through j are mixed with compound 3 and their structures are depicted above. Error bars represent one standard deviation.

DETAILED DESCRIPTIONS OF CERTAIN EMBODIMENTS

As discussed above, the present invention can comprise a composition comprising a PA compound comprising a magnetic resonance contrast agent bonded, conjugated with or otherwise coupled to a terminal or nonterminal amino acid residue of the peptide component of a PA. In certain embodiments, such a contrast agent can be conjugated to a nonterminal amino acid such that the peptide component can provide a degree of steric hindrance with respect to the chelator component of the contrast agent. Without limitation to any one theory or mode of operation, such steric hindrance can be used to substantially improve the contrast exhibited by the PACA under magnetic resonance imaging conditions. Suitable magnetic resonance contrast agents can comprise any metal ion known in the art as useful in the context of such imaging, including but not limited to manganese, iron or gadolinium, and any ligand component capable of chelation therewith. Such contrast agents include but are not limited to gadopentetate dimeglumine, gadoterate meglumine gadodiamide, gadoteridol, gadobutrol, gadoversetamide, gadobenate dimeglumine, gadoxetic acid disodium or gadophostriamine trisodium. These and other agents are known in the art and/or described in P. Caravan, et al., Chemical Reviews, vol. 99, pp. 2293-2352 (1999), which is hereby incorporated by reference in its entirety. Chelator components that can chelate gadolinium(III) and/or other such useful metal ion species, to form contrast agents useful in magnetic resonance imaging, include but are not limited to 1,4,7-tris(carboxymethyl)-10-yl-1,4,7,10-tetraazacyclododecane ("DO3A"), diethylenetriaminepentaacetate ("DTPA") octadentate hydroxypyridinonate ("HOPO") or various derivatives of 3,2-HOPO, 2,5,8-tris (carboxymethyl)-12-phenyl-11-oxa-2,5,8-triazadodecane-1, 9-dicarboxylic acid ("BOPTA"), or 1,4,7,10-tetraazacyclododecane-1,4,7,10-tetraacetic acid ("DOTA"). Magnetic resonance imaging and associated contrast agents are described in U.S. Pat. No. 6,656,450, U.S. Pat. No. 5,702,683 and U.S. Pat. No. 4,933,441, which are incorporated herein by reference in their entireties.

A PACA compound of this invention can comprise a hydrophobic moiety, which can preferably but not necessarily comprise a saturated hydrocarbon moiety such as a palmitoyl group. Those skilled in the art will recognize that the hydrocarbon moiety can, without limitation, readily be chosen from the group including capryloyl, nonanoyl, caproyl, undecanoyl, lauroyl, tridecanoyl, myristoyl, pentadecanoyl, heptadecanoyl, stearoyl, nonadecanoyl, arachidoyl, behenoyl, 13,13-dimethyltetradecanoyl and tuberculostearoyl moieties. Unsaturated fatty acid derivatives could also be suitable for use as the hydrophobic moiety; suitable groups could include but are not limited to oleoyl, linoleoyl, arachidonoyl, eicosapentaenoyl, docosahexaenoyl and eurucoyl moieties. Suitable hydrocarbon moieties can comprise any branched or unbranched, saturated or unsaturated groups comprising from about 6 carbon atoms to about 24 carbon atoms.

A PACA compound can also comprise a branched peptide component. In certain embodiments, such a component can be relatively more hydrophilic than is the hydrophobic moiety. Such a relationship can facilitate the formation of fibers or other extended structures comprising the PACA. A branched peptide portion can be constructed of any combination of naturally occurring or synthetic amino acids using conventional techniques, which may include solid phase peptide synthesis ("SPPS"). Mild orthogonal protecting group techniques may be useful in preparing the branched peptide chains. The preparation of PA's using SPPS is described in U.S. Pat. No. 6,096,863, which is hereby incorporated by reference in its entirety.

In certain embodiments, a PACA compound can be particularly useful comprising a bioactive peptide sequence as part of the peptide component. For example, without limitation, those skilled in the art will recognize that the sequence RGDS is known to be important in cell adhesion. In certain embodiments, inclusion of an RGD sequence within the PACA structure can facilitate the function of the PACA as a scaffold for tissue repair. The synthesis of polypeptides comprising the RGD amino acid sequence for purposes of promoting cell adhesion is described in U.S. Pat. No. 5,840,691, U.S. Pat. No. 5,019,646 and U.S. Pat. No. 4,839,464, which are hereby incorporated by reference in their entireties. Those skilled in the art will recognize that the amino acid sequence used in the present invention for purposes of promoting cellular adhesion is extendible to other amino acid sequences which are known to promote or may be found to promote cellular adhesion in the context of tissue repair.

In part, this invention can also be directed to compositions or assemblies comprising one or more PACAs in combination with a PA or PAs that lack a magnetic resonance imaging contrast agent moiety. Without limitation, such PA or PAs can have component structures at least in part similar to that of the PACA used; that is, having a structural or compositional similarity to the portion of the PACA structure extraneous to the ligand chelating the metal ion of the contrast agent. Such PA or PAs can be different in structure as compared to any portion of the PACA structure; that is, the extent of peptide chain branching or the identities of epitope sequences incorporated within the structures of such PA or PAs need not be similar to those found in any PACA of a corresponding composition. Accordingly, compositions of the present invention can comprise one or more PAs with peptide components unbranched or comprising one or more branches. The preparation of PA's and their assembly into extended structures is described in U.S. Pat. No. 6,096,863, referenced above, and U.S. Pat. No. 5,955,343, which is hereby incorporated by reference.

Those skilled in the art will recognize that the general scheme imparting susceptibility to mapping by magnetic resonance imaging within a macromolecular scaffold structure suitable for tissue repair to the above compositions may readily be applied to other extended structures and that the invention is not limited to extended structures derived from PAs. Extended structures that may serve as tissue repair scaffolds include, without limitation, those capable of forming hydrogels, including, without limitation, collagen, gelatin, hyaluronate, fibrin, alginate, agarose, chitosan, poly(acrylic acid), poly(ethylene oxide), poly(vinyl alcohol) and polyphosphazine. Such hydrogels are described in K. Y. Lee & D. J. Mooney, Chemical Reviews, vol. 101, pages 1869-79 (2001), which is hereby incorporated by reference.

Likewise, the general scheme of the present invention can apply when methods other than magnetic resonance imaging are used to map the locations of scaffold nanofibers or biological cells within networks of such nanofibers. For example, a radioactive nuclide appended to a PA could be imaged using positron emission tomography ("PET"). Alternatively, PAs of the present invention may be tracked using computed tomography ("CT" or "CAT").

In part, this invention can be directed to compounds, compositions and/or assemblies of the sort described above, further comprising one or more epitopes or amino acid sequences targeted to interact with specific cellular receptors. Such epitope-bearing PAs can be incorporated into extended structures and nanofibers in order to study the effects of various epitopes on the progress of nanostructured tissue repair. This can be done without the need to synthesize an effective new PACA for each experiment. In certain embodiments, such epitope-bearing PAs can, but need not comprise hydrophobic moieties and/or amino acid sequences that are at least in part structurally similar to those used in the preparation of the PACA and other PAs of the nanofiber. Without limitation, such nanofiber structures will not be substantially affected by the presence of epitope-bearing PAs, and the effects of various epitopes on nanofiber fate and tissue repair may be studied in isolation. Epitopes of interest in this context may include, without limitation, the amino acid sequences IKVAV and YIGSR as well as RGD. PAs that have a bioactive epitope sequence and are capable of forming a sol-gel system are described in pending published U.S. Patent Application No. 20040001893, which is hereby incorporated by reference.

In part, this invention can provide a method for using magnetic resonance imaging in conjunction with compositions of the sort described above to map the fate of extended structures such as nanofibers used as tissue-engineered scaffolds in vivo. Such methods may be used in conjunction with the repair of bone, cartilage, or other tissue of humans or animals, to allow a researcher or medical practitioner to identify the precise locations where construction of new tissue is occurring and, qualitatively, the extent to which construction of new tissue is occurring at each location. Fate mapping of extended structures or epitope-bearing nanofibers over time and three dimensional space may yield new insights into healing processes and rates and may allow the injection of additional tissue regenerating scaffold composition to the locations where such injection shall be determined to have the greatest value. The end result could be faster healing of bone fractures and faster post-operative healing in many surgical procedures. As such, a method of the present invention may be useful in the investigation and treatment of diabetes. Without limitation, PA scaffolds can encapsulate beta-islet cells, and magnetic resonance imaging may be useful in tracking both the scaffolds and the beta-islet cells.

More specifically, with reference to FIGS. 1-4 and compounds 1-3, a non-limiting representative Gd(III) chelator is a DOTA derivative—selected because of its high binding constant for lanthanides and synthetic versatility. (See, Caravan, P., Ellison, J. J., McMurry, T. J., and Lauffer, R. B. (1999) Gadolinium(III) Chelates as MRI Contrast Agents Structure, Dynamics, and Applications. *Chem. Rev.* 99, 2293-2352.) PA 1 is a self-assembling PA that forms self-supporting gels and is similar in sequence to PACA's 2 and 3 but does not contain the Gd(III) chelator and thus was used as a standard to compare to the MR images of the gels with Gd(III). (See, FIG. 1) Gels of 1 and 2, or 1 and 3, were prepared to demonstrate a minimal concentration of peptide amphiphile contrast agent (PACA) for good MR contrast, allowing other PA molecules of a composition or gel to present one or more different epitopes in conjunction with the resulting nanofibers. Varying the position of the tethered DOTA derivative on the PAs induces changes in the molecule's relaxivity (efficiency) and imaging utility. The PACA derivatives described contain the RGD peptide sequence, a well-known epitope in integrin-binding domains of extracellular proteins, for adhesion of many types of cells to the extracellular matrix. Positioning the chelate close to the hydrophobic end of the molecule can result in a higher relaxivity. PACAs 2 and 3 differ in the position of the Gd(III) chelator, that results in a change in relaxivity in the self-assembled state from 14.7 $mM^{-1}s^{-1}$ to 21.5 $mM^{-1}s^{-1}$, respectively (normalized to ICP measurements of Gd(III) concentration) in a buffer solution at pH 7.41. Without restriction as to any one theory or mode of operation, the difference in relaxivity between 2 and 3 can be due to a difference in the rotational correlation time, $\tau_r$, arising from decreased internal flexibility and increased steric hindrance of the chelator in 3 as compared to 2.

Transmission electron microscopy (TEM) and atomic force microscopy (AFM) reveal the supramolecular structural aggregates from 1, 2, and 3 (FIG. 2). Both PACA's 2 and 3 self-assemble into fibers at pH greater than 7.0 and 1-3 form uniform nanofibers microns in length. The fiber diameter of structures formed by PACA 3 was calculated from AFM height measurements to be 6.0±0.1 nm with 95% confidence. A self-supporting gel is formed upon mixing PACA's 2 or 3 with PA 1, followed by ultrasonication and buffer addition. Circular dichroism (CD) spectroscopy was used to probe the hydrogen bonding interaction in the supramolecular polymer to compare with the structural observations in dried films obtained by TEM and AFM. The minima of PACA's 2 and 3 without Gd(III) reveal a peak at 212 nm, signifying a β-sheet like hydrogen bonding character, which supports fiber formation in the samples seen by AFM and TEM. These shifts in spectra from ideal β-sheets are thought to be from the change in hydrogen bonding caused by both the chelator and the branching motif used in synthesis.

Mixing PACAs 2 or 3 with filler PA 1 could be successfully imaged by MR (FIG. 3). The gels are homogeneous in image intensity throughout the samples, which implies uniform mixing of the PACA molecules within the filler PA at MR resolution. If heterogeneous mixing of PAs occur on a large enough scale, domains of bright and dark intensity would be observed. FIG. 3 shows the difference in observed contrast between 1 (without Gd(III)), 2 mixed with 1, 3 mixed with 1, and a standard small molecule MR contrast agent diethylenetriaminepentaacetate (DTPA) doped into 1 (0.1 mM Gd(III)). The gels were made using a 0.75 wt. % of filler PA. The PACA molecule was mixed into this solution before gelling as was the DTPA. Images were acquired using a spin-echo pulse sequence with TR 750 ms, TC 12 ms, slice thickness of 1 mm, FOV of 2 cm, at 9.4 T on an Oxford superconducting magnet and Bruker software. The $T_1$ of these gels were measured at 3.03±0.05 s, 1.89±0.06 s, 1.08±0.06 s, and 2.81±0.05 s, respectively, the faster $T_1$'s resulting in higher contrast. Such results clearly demonstrate the utility of using a contrast agent with a high relaxivity for imaging biomaterials.

Without limitation, a PACA of this invention can mix homogeneously with a variety of different epitope-containing PA's, to simplify in vivo tests for fate mapping of different gels and allow for differing biomaterial specificity and bioactivity without synthesizing a new PACA for every material. The ubiquitous nature of compound 3, owing to its higher relaxivity, was tested with a range of differing PAs chosen for variation in structure, epitope(s), and sequence terminus (either C-terminus or N-terminus). With reference to FIG. 4, h-j, are all linear PA's synthesized C— to N-terminus with an IKVAV epitope used for neuronal stem cell differentiation. Structures e and f are branched PA's containing the IKVAV epitope, and e contains the YIGSR epitope as well also for use in neuronal stem cell differentiation. Structure g is branched and contains the RGD epitope for cell adhesion. All samples formed aqueous self-supporting gels at 1 wt % and were imaged in a 400 MHz magnet. All of the gels imaged were of homogeneous signal intensity, and the $T_1$'s of the gels were all similar values when doped with equal amounts of 3 (FIG. 4), showing the robustness and consistency of 3 and its ability to be used in differently structured and epitope presenting biomaterials.

As demonstrated above, the ability to noninvasively image gels formed by scaffolds of PA nanofibers doped with self-assembling PACA molecules provides a means for in vivo fate mapping of these new biomaterials. Comparing two PACA molecules differing in the position of a chelator component, a variety of mixed systems can be used to elucidate a minimal amount of a PACA needed to achieve a homogeneous and significant signal intensity. More specifically, placing a Gd(III) chelator component closer to the hydrophobic region of the self-assembling molecules provides an increase in relaxivity. Accordingly, PACA 3—representative of other such amphiphilic peptide compounds—can be used with a variety of different PA compounds to provide a range of corresponding compositions, micellar configurations and/or hydrogels.

EXAMPLES OF THE INVENTION

The following non-limiting examples and data illustrate various aspects and features relating to the compounds and compositions of the present invention, including the self-assembly of amphiphilic peptide compositions, as can be achieved through the synthetic techniques and methodologies described herein. In comparison with the prior art, the present compounds and/or compositions provide results and data which are surprising, unexpected and contrary thereto. While the utility of this invention is illustrated through the use of several compositions, compounds and/or components thereof, it will be understood by those skilled in the art that comparable results are obtainable with various other compositions, compounds and/or components thereof, as are commensurate with the scope of this invention.

Example 1a

Preparation of compounds 1-3. Amino acids were purchased from NovaBiochem. All other reagents were purchased from Sigma-Aldrich and used without further purification unless otherwise stated. The branched PA's 1, 2 and 3 were prepared by 9-fluorenylmethoxycarbonyl (Fmoc) solid-phase peptide synthesis (SPPS) on a 0.1 mmol scale, as would be known in the art by those made aware of this invention.

Various branched peptide amphiphile compounds used in conjunction with the present invention together with any one or more of the preceding considerations, can be synthesized using preparatory techniques well-known to those skilled in the art, including those disclosed in co-pending application Ser. Nos. 11/005,314 and 11/005,552 filed on Dec. 6, 2004 (International Publication Nos. WO 05/056576 and WO 05/056039, respectively), each of which are incorporated herein by reference in their entirety, and modifications of those techniques known in the literature and as referenced elsewhere herein. The synthetic schemes, including peptide and hydrophobic components, coupling/branching residues and/or moieties thereof and epitope sequences described, set forth or inferred in such references and co-pending applications may be applied to the present invention. Peptide amphiphiles may be fully protonated, partially protonated, or as acid or basic addition salts. Generally, such peptide amphiphiles can be prepared using standard solid-phase peptide chemistry including addition of a hydrophobic tail or component at or near the C-terminus of the peptide component. Modifications of such synthetic techniques can be made as would be known to those skilled in the art and aware of this invention, such as by using procedures and the corresponding peptide amphiphile moieties, compounds, related compositions, and configuration or assemblies described in co-pending application Ser. No. 10/294,114 filed Nov. 14, 2002 (International Publication No. WO 03/054146) and Ser. No. 10/368,517 filed Feb. 18, 2003 (International Publication No. WO 03/070749), each of which is incorporated herein by reference in its entirety.

Example 1b

PA 1 was prepared by SPPS, and branching of the peptide headgroup was achieved using orthogonal protecting group chemistry for the amines at the α and ε positions of the lysine residue. Fmoc-Lys(Mtt)-OH (Mtt: 4 methyltrityl) was coupled to MBHA Rink Amide resin, followed by cleavage of the Mtt protecting group on the ε-amine to couple palmitic acid without affecting Fmoc protection with a 5% TFA in DMF solution for 5 min. This was followed by Fmoc removal on the α-amine to grow the LLLAAA peptide segment of the PA using 30% piperidine/DMF solution for 10 min. The branching point was introduced at a lysine dendron using Fmoc-Lys(Mtt)-OH. To grow the first arm of the PA, Fmoc on the α-amine was removed before Mtt. L-Aspartic acid di-tert-butyl ester hemisuccinate residue was coupled to the first branch. Mtt on the ε-amine of the lysine residue was removed, and bioactive peptide sequence RGDS was grown. Aspartic acid residue before the RGDS was coupled to increase solubility of the molecule in water. PA 1 was cleaved from the resin in 95:2.5:2.5 TFA:TIS:$H_2O$. Excess TFA was evaporated under reduced pressure and crude PA solutions were triturated using cold ether. MALDI-TOF mass spectroscopy 1810.40 (calcd 1810.14)

Example 1c

PACA's 2 and 3 were synthesized using orthogonal protection group chemistry for the amines at the α and ε positions of the lysine residue. Fmoc-Lys(Mtt)-OH was coupled to MBHA Rink Amide resin, followed by cleavage of the Mtt protecting group on the ε-amine for palmitic acid coupling without affecting the Fmoc protection. This was followed by Fmoc removal on the α-amine to extend the peptide segment of the PA. The branching point in the PA's was introduced at a lysine dendron using Fmoc-Lys(Mtt)-OH. To extend the first arm of PA's, Fmoc on the α-amine was removed before Mtt. For molecule 2, Boc-Lys(Boc)-OH was coupled at the end of the first branch. Both α and ε-amine positions of the lysine were blocked with Boc protection as it is more stable under the cleavage conditions employed for the removal of Fmoc and Mtt. For 3, Boc-Lys(Fmoc)-OH was coupled as the first branch. Fmoc was deprotected and tris-tert-butyl-protected 1,4,7,10-tetraazacyclododecane-1,4,7,10 tetraacetic acid (DOTA) (purchased from Macrocyclics) was coupled at the end of the first branch. Mtt was removed, and the other branch was grown using Boc-Lys(Fmoc)-OH. The peptide sequence RGDS was coupled to the ε-amine in order to combine bioactivity and MR functionality. For 2, the DOTA moiety was coupled on SPPS to the N-terminus of the peptide sequence by using a tert-butyl ester-protected DOTA molecule. Compounds 2 and 3 were cleaved from the resin in 95:2.5:2.5 TFA:TIS:$H_2O$. Excess TFA was evaporated under reduced pressure, and crude PA solutions were triturated using cold ether. Compounds 2 and 3 were purified by reverse phase HPLC, then dried under vacuum and characterized by MALDI-MS with a single peak found at 2308.66 (calcd 2308.87) and 2180.02 (calcd 2179.69), respectively. The final product was obtained by the addition of $GdCl_3$ with stirring at pH 6.5 for 72 h and purified by dialysis in deionized water (1000MWC Spectrum Laboratories Inc.). Samples were then lyophilized into a white powder. MALDI-MS showed peaks at 2464.40 (calcd 2463.09) and 2336.08 (calcd 2335.61) corresponding to 2 and 3 M+H, respectively.

Example 2

Inductively Coupled Plasma Mass Spectrometry. Inductively coupled plasma mass spectrometry (ICP-MS) was performed on a Thermo Jarrell Ash Atomscan Model 25 Sequential ICP Spectrometer. Samples were prepared by taking an aliquot of 2 and 3 from the stock solution used for relaxivity and $T_1$ measurements and placed in 600 μL of neat nitric acid. Five milliliters of deionized water was added, and the solution was ultrasonicated for 3 min. The volume was brought up to 9990 μL with deionized water, and 10 μL of an indium standard was added to bring the total volume to 10 mL Example 3

Relaxivity Measurements. Relaxivity measurements were performed on 2 and 3 by reconstituting the samples in deionized water to form stock solutions, and the relaxivity experiments were performed on a Bruker mq60 NMR Analyzer (Bruker Canada, Milton, Ont., Canada) in pH 7.41 buffer at 37 C (10 mM 3-(N-morpholino)propanesulfonic acid (MOPS), 100 mM sodium chloride, 20 mM sodium bicarbonate, and 4 mM sodium phosphate monobasic). Four samples were prepared of each of PACA's 2 and 3 at concentrations of about 0.005, 0.01, 0.015, 0.02 mM (actual concentrations of Gd(III) were calculated from ICP-MS). Measurements were performed in quadruplicate and plotted as $1/T_1$ vs. mM Gd(III). The slope of this line provides the molar relaxivity.

Example 4

$T_1$ Measurements. $T_1$ measurements were performed on a 9.4 T Oxford superconducting magnet (Bruker). The samples were prepared by making a 4 wt % solution of PA 1 in water. This solution was then aliquoted into four separate 3-dram vials. The appropriate amount of Gd(III)-containing molecules in aqueous solution was added to each vial to bring the concentration of Gd(III) to 0.1 mM (normalized to ICP measurements of Gd(III) concentration). Excess water was added to bring the total volume to 250 μL. These solutions were ultrasonicated for 30 s and transferred to 5 mm NMR tubes. Fifty microliters of 0.1 M calcium carbonate buffer was added to each tube to increase the pH and induce gelation. Four sample tubes were bound together using Parafilm wax and inserted into the magnet. Images were acquired using a spin-echo pulse sequence with TR of 152, 200, 400, 750, 1000, 1400, 1800, 2500, 4000, 10 000 ms, TE 12 ms, slice thickness of 1 mm (eight slices taken), and FOV of 2 cm.

Example 5

Circular Dichroism. Circular dichroism (CD) was performed on a Jasco J-715 CD spectrophotometer using a 2 mm quartz cuvette. Samples were prepared from the stock solution in water to a final concentration of $3.33 \times 10^{-6}$ M at a pH of 7.4 in PBS buffer. Five spectra from 190 to 260 nm were averaged together.

Example 6

AFM. AFM preparation was from the same stock solutions of compounds 1-3 (0.005 mM) that were used to determine relaxivity, diluted 1:10 with deionized water. Samples were prepared by drop casting 5 μL of the diluted solutions onto freshly cleaved mica substrates. Samples were allowed to rest for 2 min before excess solution was wicked away. After drying in air, AFM was performed with a Digital Instruments MultiMode III SPM with a Quadrex extender and Olympus AC240TS cantilevers in tapping mode. Height measurements were taken on 149 straight fiber segments using the cross-sectional averaging tool included in Digital Instruments Nanoscope III acquisition analysis software.

We claim:

1. A composition comprising a plurality of different amphiphilic peptide compounds, each said compound comprising a peptide component and a hydrophobic component comprising a hydrocarbon moiety selected from about $C_6$ to about $C_{24}$ linear alkyl moieties and about $C_6$ to about $C_{24}$ branched alkyl moieties, said hydrocarbon component coupled to said peptide component at one of the C-terminus and N-terminus thereof; and at least one said compound a branched amphiphilic peptide compound comprising a peptide component comprising residues selected from alanine, glycine, cysteine, leucine and combinations thereof and at least one amino acid residue comprising a pendant amino group coupled to a portion of said peptide component non-linear thereto, and at least one amino acid residue comprising a pendant amino group conjugated with a chelator component of a gadolinium, iron or manganese magnetic resonance contrast agent, said chelator component at a position on said peptide component not at the end of said non-linear portion.

2. The composition of claim 1 wherein said chelator component is conjugated with a residue of said non-linear portion.

3. The composition of claim 2 wherein at least one of said conjugation residue and said coupling residue is of lysine.

4. The composition of claim 1 wherein said chelator component is selected from DO3A, DTPA, HOPO, BOPTA and DOTA.

5. The composition of claim 4 wherein said chelator component is DOTA.

6. The composition of claim 5 comprising gadolinium ion.

7. The composition of claim 6 wherein said conjugation residue is of lysine.

8. The composition of claim 1 wherein said non-linear portion comprises a bioactive epitope sequence selected from RGDS, IKVAV, YIGSR and combinations thereof.

9. The composition of claim 1 in an aqueous medium and assembled in a micellar configuration.

10. The composition of claim 9 imaged in a magnetic field.

11. A composition comprising a plurality of different amphiphilic peptide compounds, each said compound comprising a peptide component and a hydrophobic component comprising a hydrocarbon moiety selected from about $C_6$ to about $C_{24}$ linear alkyl moieties and about $C_6$ to about $C_{24}$ branched alkyl moieties, said hydrocarbon component coupled to said peptide component at one of the C-terminus and N-terminus thereof; and at least one said compound a branched amphiphilic peptide compound comprising a peptide component comprising residues selected from alanine, glycine, cysteine, leucine and combinations thereof, a gadolinium magnetic resonance contrast agent having a chelator component conjugated to said peptide component with a lysine residue, and a branch portion of said peptide component non-linear to said peptide component, said branch portion coupled to said peptide component with a lysine residue and comprising a bioactive epitope sequence selected from RGDS, IKVAV, YIGSR and combinations thereof, said contrast agent not on said branch portion.

12. The composition of claim 11 wherein said chelator component of said contrast agent is DOTA.

13. The composition of claim 11 wherein a said alkyl moiety is coupled to a lysine residue at about the C-terminus of said peptide component.

14. The composition of claim 11 in an aqueous medium at a physiological pH and assembled in a cylindrical micellar configuration.

15. The composition of claim 14 imaged in a magnetic field.

16. A branched amphiphilic peptide compound of a formula

wherein $X_1$ is a gadolinium magnetic resonance contrast agent comprising a chelator component, $X_2$ is a branch portion of said peptide component comprising a bioactive epitope sequence selected from RDGS, IKVAV, YIGSR and combinations thereof, and C is a hydrophobic component comprising an alkyl moiety selected from about $C_6$ to about $C_{24}$ linear alkyl moieties and about $C_6$ to about $C_{24}$ branched alkyl moieties.

17. The compound of claim 16 wherein said chelator component is DOTA.

18. The compound of claim 16 in a hydrogel comprising at least one other amphiphilic peptide compound.

* * * * *